United States Patent [19]

Hirsbrunner et al.

[11] Patent Number: 4,758,662

[45] Date of Patent: * Jul. 19, 1988

[54] PURIFICATION OF CAFFEINE

[75] Inventors: Pierre Hirsbrunner, Corseaux; Blaise Pavillard, Fribourg, both of Switzerland

[73] Assignee: Nestec S. A., Vevey, Switzerland

[*] Notice: The portion of the term of this patent subsequent to Jul. 23, 2002 has been disclaimed.

[21] Appl. No.: 15,549

[22] Filed: Feb. 13, 1987

Related U.S. Application Data

[63] Continuation of Ser. No. 727,219, Apr. 25, 1985, abandoned, which is a continuation of Ser. No. 479,791, Mar. 23, 1983, Pat. No. 4,531,003, which is a continuation of Ser. No. 254,100, Apr. 14, 1981, abandoned.

[51] Int. Cl.$^4$ .............................................. C07D 473/12
[52] U.S. Cl. ..................................... 544/275; 544/274
[58] Field of Search ................................. 544/274, 275

[56] References Cited

U.S. PATENT DOCUMENTS

| | | | |
|---|---|---|---|
| 1,235,278 | 7/1917 | Barr | 544/275 |
| 2,508,545 | 5/1950 | Shuman | 544/274 |
| 2,785,163 | 3/1957 | Swidinsky | 544/275 |
| 3,321,142 | 5/1967 | Knahnefeld | 544/275 |
| 4,380,631 | 4/1983 | Bott | 544/275 |

OTHER PUBLICATIONS

Merck Index 9th Edition, 1976, p. 207.

*Primary Examiner*—Robert J. Warden
*Assistant Examiner*—Robert Benson
*Attorney, Agent, or Firm*—Vogt & O'Donnell

[57] ABSTRACT

A process for the purification of caffeine which comprises carrying out the following steps in any order;
 (a) recrystallization of caffeine from an aqueous alkaline solution of caffeine containing a reducing agent and
 (b) extraction of the caffeine from an aqueous alkaline solution of caffeine with a substantially water-immiscible solvent which is liquid under the conditions of the process.

13 Claims, No Drawings

PURIFICATION OF CAFFEINE

This application is a continuation of application Ser. No. 727,219, filed Apr. 25, 1985, now abandoned, which is a continuation of Ser. No. 479,791, now U.S. Pat. No. 4,531,003, filed Mar. 23, 1983, which was a continuation of Ser. No. 254,100, filed Apr. 14, 1981, now abandoned.

BACKGROUND OF THE INVENTION

The present invention relates to a process for the purification of caffeine, more particularly to the production of caffeine in crystalline form which is sufficiently pure for use in pharmaceuticals and foodstuffs. Caffeine produced industrially by the decaffeination of green coffee is generally rather crude, containing approximately 85% caffeine, and is unsuitable for use in pharmaceuticals or foodstuffs.

Several attempts have been made to purify caffeine. For example, sublimation has been tried but the yield was poor due to chemical decomposition. Purification by recrystallisation from water has also been tried but the morphology of the crystals (long needles forming inextricable masses) caused the retention of impure mother-liquor and the chemical nature of the caffeine caused associations with the impurities, preventing the formation of a pure solid phase. Even after four successive recrystallisations a product of the desired purity was not obtained.

SUMMARY OF THE INVENTION

We have found, surprisingly, that if the recrystallisation is carried out from an aqueous solution containing an alkali and certain reducing agents a very pure product can be obtained. In addition if the caffeine is extracted from an aqueous solution containing an alkali by certain water-immiscible organic solvents either before or after recrystallisation a very high yield can be achieved.

Accordingly, the present invention provides a process for the purification of caffeine by preparing an aqueous alkaline solution of crude caffeine and then reducing the impurities of the crude caffeine in the aqueous alkaline medium and, before or after this step, extracting caffeine with a substantially water-immiscible liquid solvent. Thus the following steps may be carried out in any order;

(a) recrystallisation of caffeine from an aqueous alkaline solution of caffeine containing a reducing agent and (b) extraction of the caffeine from an aqueous alkaline solution of caffeine with a substantially water immiscible solvent which is liquid under the conditions of the process.

DESCRIPTION OF PREFERRED EMBODIMENTS

For convenience, the expression "aqueous alkaline solution of caffeine" in this invention refers to any aqueous solution of caffeine containing alkali even if the pH is less than 7.

The pH of the aqueous alkaline solution of the caffeine is conveniently at least 6.5 and preferably from 8 to 10.

The alkali that is contained in the aqueous solution of the caffeine may be any compound, compatible with use in a food environment, that can increase the pH of an aqueous caffeine solution to the desired value. It is preferably inorganic and may be, for example, an alkali metal hydroxide such as sodium hydroxide or potassium hydroxide. The amount used and the concentration of the alkali are conveniently chosen to achieve the desired pH. For example a 30% solution of an alkali metal hydroxide may be used in an amount of from 1 to 20%, preferably from 2.5 to 10% by weight, based on the weight of crude caffeine.

The reducing agent should be of low toxicity, compatible with its use in a food environment. The reducing agent, which is non-reactive with caffeine and reduces the impurities of the crude caffeine and is thus oxidized, should be soluble in its oxidized form in the aqueous alkaline medium. While sulphites may be used, a dithionite such as sodium dithionite, or zinc powder is preferred. The amount of reducing agent may vary widely but usually depends on the particular reducing agent used. For example, a dithionite may be used in an amount of from 2.5 to 15%, preferably from 4 to 10% by weight, based on the weight of crude caffeine, whereas zinc powder may be used in an amount from 0.1 to 10% and preferably from 0.25 to 2.5% by weight based on the weight of crude caffeine.

Desirably, the recrystallisation is carried out in the presence of an inert protecting gas which may be, for example, helium, neon, argon or methane but is preferably nitrogen.

The concentration of caffeine in the aqueous alkaline solution may vary widely, for example, from 5 to 50% but for economic reasons is usually from 7.5 to 25% by weight based on the weight of water.

The temperature of the aqueous alkaline solution of the caffeine is preferably high enough to dissolve all the caffeine present and is conveniently from 50° to 100° C. preferably from 60° to 80° C. Recrystallisation takes place by cooling, conveniently to a temperature below 30° C. and preferably to a temperature from 15° to 25° C.

The solvent used for the extraction of the caffeine from the aqueous alkaline solution conveniently has a boiling point of from 35° to 100° C. and is preferably non-toxic and non-inflammable. The most suitable solvents are halogenated hydrocarbons, preferably chlorinated hydrocarbons, for example, dichloromethane. The extraction is preferably carried out at a temperature at or in the vicinity of the boiling point of the solvent. The amount of solvent used may vary widely and may be from 0.5 to 100 parts and preferably from 1 to 10 parts by weight per part by weight of the aqueous alkaline solution. The extraction of the caffeine with the solvent may suitably take place in a counter-current manner. If the caffeine is extracted after the recrystallisation, it is extracted from the aqueous alkaline solution filtered off from the recrystallised caffeine. If the caffeine is extracted before the recrystallisation, it is preferably extracted from an aqueous alkaline solution of caffeine in the absence of a reducing agent, after which the solvent phase containing the caffeine is separated from the aqueous phase, the solvent evaporated off and the caffeine dissolved in fresh aqueous alkaline solution containing a reducing agent and subsequently recrystalised. The extraction may conveniently be carried out by a continuous process. Preferably the extraction of the caffeine from the aqueous alkaline solution is carried out before the recrystallisation.

By recycling the aqueous alkaline solution containing caffeine and sujecting it to one or more further recrystallisations and extractions it is possible to increase the yield of very pure caffeine. The whole process may be carried out continuously, if desired. Particularly when subjecting the aqueous alkaline solution to one or more further recrystallisations and extractions, the reducing agent utilized, in it oxidized form, is soluble in the aqueous alkaline medium.

The process of the present invention is preferably carried out at atmospheric pressure. The process can be used to purify caffeine obtained from any source and can easily be adapted to operate in a coffee-manufacturing plant.

The following Examples further illustrate the present invention.

EXAMPLE I 100 g of crude industrial caffeine containing 84.8 g caffeine were dissolved in1 liter of an aqueous solution containing 6 ml of a 30% solution of sodium hydroxide and having a pH of 9 and a temperature of 70° C. To this solution were added 10 g of active charcoal, 5 g of sodium dithionite and 4 g of celite. Nitrogen was bubbled through and after mixing, the solution was filtered to remove the active charcoal celite and impurities.

The filtrate was then cooled to 20° C. to recrystallise some of the caffeine. The crystals were filtered off and washed with 200 ml of washing water. The mother-liquor, which was an aqueous alkaline solution containing the remainder of the caffeine, together with the washing water, were extracted with 2 liters of dichloromethane at 40° C. in a countercurrent manner. The dichloromethane phase containing most of the caffeine was separated from the impure exhausted aqueous alkaline phase and the dichloromethane was evaporated off to yield a further quantity of caffeine, which together with the previously recrystallised caffeine weighed 55 g. This caffeine was added to a mixture of 500 g of fresh water and 1 g of sodium dithionite at 70° C. and the pH was adjusted to 9 by further addition of 1.2 ml of 30% sodium hydroxide. Nitrogen was bubbled through and after mixing, the temperature was reduced to 20° C. to recrystallise some more of the caffeine. The crystals were filtered off, washed with 200 ml of fresh washing water and dried to give 30 g of pure caffeine. The mother-liquor, which was an aqueous alkaline solution containing the remainder of the caffeine, together with the washing water, were recirculated and extracted at 40° C. with the dichloromethane which had been evaporated off after the first extraction. The dichloromethane phase containing most of the caffeine was separated from the impure aqueous alkaline phase and the dichloromethane was evaporated off and the caffeine recrystallised again as before. This recirculation of the mother-liquor and dichloromethane, and the recrystallisation of the caffeine followed by drying were repeated until the yield of pure caffeine was 95%.

EXAMPLE 2

100 g of crude industrial caffeine containing 84.8 g caffeine were dissolved in 500 g of an aqueous solution containing 6 ml of a 30% solution of sodium hydroxide and having a pH of 9 and a temperature of 70° C. To this solution were added 10 g of active charcoal, 1 g of powdered zinc and 4 g of celite. Nitrogen was bubbled through and after mixing, the solution was filtered to remove the active charcoal, celite and impurities.

The filtrate was then cooled to 20° C. to recrystallise some of the caffeine. The crystals were filtered off and washed with 300 ml of washing water. The mother-liquor, which was an aqueous alkaline solution containing the remainder of the caffeine, together with the washing water, were extracted with 1 liter of dichloromethane at 40° C. in a countercurrent manner. The dichloromethane phase containing most of the caffeine was separated from the impure exhausted aqueous alkaline phase and the dichloromethane was evaporated off to yield a further quantity of caffeine which together with the previously recrystallised caffeine weighed 44 g. This caffeine was added to a mixture of 850 g of fresh water and 0.4 g of powdered zinc at 70° C. and the pH was adjusted to 9 by the further addition of 0.8 g of 30% sodium hydroxide. Nitrogen was bubbled through and after mixing, the temperature was reduced to 20° C. to recrystallise some more of the caffeine. The crystals were filtered off, washed with 300 ml of fresh washing water and dried to give 41 g of pure caffeine. The mother-liquor, which was an aqueous alkaline solution containing the remainder of the caffeine, together with the washing water, were recirculated and extracted at 40° C. with the dichloromethane which had been evaporated off after the first extraction. The dichloromethane phase containing most of the caffeine was separated from the impure aqueous alkaline phase and the dichloromethane was evaporated off and the caffeine recrystallised again as before. This recirculation of the mother-liquor and dichloromethane, and the recrystallisation of the caffeine followed by drying were repeated until the yield of pure caffeine was 95%.

EXAMPLE 3

100 grams of crude industrial caffeine containing 84.8 g caffeine were dissolved in 1 liter of an aqueous solution containing 6 ml of a 30% solution of sodium hydroxide and mixed at 40° C. before filtering to remove the pellicules. The aqueous phase was then extracted with 2 liters of dichloromethane at 40° C. in a countercurrent manner up to exhaustion of the caffeine. The dichloromethane phase containing most of the caffeine was separated from the impure aqueous alkaline phase and the dichloromethane was evaporated off leaving 74 g of caffeine. This caffeine was then redissolved in 1100 g of fresh water at 70° C. and 0.4 g of a 30% solution of sodium hydroxide was added to bring the pH to 9.5. 10 g of activated charcoal, 0.4 g of zinc powder and 4 g of celite were then added and nitrogen was bubbled through. After mixing the solution was filtered to remove the zinc, activated charcoal, celite and impurities. The filtrate was then cooled to 20° C. to recrystallise some of the caffeine. the crystals were filtered off, cleaned with 300 ml of fresh washing water and dried to give 46 g of pure caffeine. The mother-liquor which was an aqueous alkaline solution containing the remainder of the caffeine was recirculated and extracted at 40° C. with the dichloromethane which had been evaporated off after the first extraction. The dichloromethane phase containing most of the caffeine which was present in the mother-liquor was separated from the impure aqueous alkaline phase and the dichloromethane was evaporated off and the caffeine recrystallised again as before. This recirculation of the mother-liquor and dichloromethane, and the recrystallisation of the caffeine followed by drying were repeated until the yield of pure caffeine was 95%. The mother-liquor and the washing water can be used to dissolve a fresh charge of crude caffeine and the process repeated.

We claim:

1. A process for purifying caffeine having impurities which comprises the steps of:

(a) preparing an aqueous solution of caffeine having impurities, wherein the solution has a pH of at least 6.5;
(b) adding a reducing agent to the solution, the reducing agent being non-reactive with caffeine and being, in its oxidized form, soluble in the solution, to reduce and be oxidized by the impurities and then recrystallizing and removing caffeine from the solution; and then
(c) extracting the solution with a substantially water-immiscible solvent for removing caffeine remaining in the solution whereby a solvent phase containing extracted caffeine and an aqueous phase are formed, separating the solvent phase from the aqueous phase and evaporating the solvent from the extracted caffeine.

2. A process according to claim 1 further comprising repeating the steps at least one more time utilizing the recrystallized and the extracted caffeine for further purifying the caffeine.

3. A process for purifying caffeine having impurities which comprises the steps of:
(a) preparing an aqueous solution of caffeine having impurities, wherein the solution has a pH of at least 6.5;
(b) extracting caffeine from the solution with a substantially water-immiscible solvent whereby a solvent phase containing extracted caffeine and an aqueous phase are formed, separating the solvent phase from the aqueous phase and evaporating the solvent from the extracted caffeine;
(c) preparing an aqueous solution of the extracted caffeine wherein the extracted caffeine solution has a pH of at least 6.5 and then adding a reducing agent to the extracted caffeine solution, the reducing agent being nonreactive with caffeine and being, in its oxidized form, soluble in the extracted caffeine solution, to reduce and be oxidized by the impurities of the caffeine and then recrystallizing and removing caffeine from the extracted caffeine solution.

4. A process according to claim 3 further comprising the step of extracting the extracted caffeine solution from which caffeine was recrystallized with a substantially water-immiscible solvent whereby a solvent phase containing extracted caffeine and an aqueous phase are formed, separating the solvent phase from the aqueous phase and evaporating the solvent from the extracted caffeine.

5. A process according to claim 4 further comprising repeating the steps at least one more time with the recrystallized and the extracted caffeine for further purifying the caffeine.

6. A process according to claim 1 or 3 wherein the pH of each aqueous solution is from 8 to 10.

7. A process according to claim 6 wherein each aqueous solution is prepared with an alkali metal hydroxide.

8. A process according to claim 1 or 3 wherein the caffeine is crystallized in the presence of an inert gas.

9. A process according to claim 6 wherein the inert gas is nitrogen.

10. A process according to claim 1 or 3 wherein the concentration of caffeine in each aqueous solution is from 7.5% to 25% by weight based on the weight of water.

11. A process according to claim 1 or 3 wherein the temperature of each aqueous solution is from 60° C. to 80° C.

12. A process according to claim 1 or 3 wherein the extraction solvent is a chlorinated hydrocarbon.

13. A process according to claim 1 or 3 wherein the extraction solvent is dichloromethane.

* * * * *

UNITED STATES PATENT AND TRADEMARK OFFICE
CERTIFICATE OF CORRECTION

PATENT NO. : 4,758,662

DATED : July 19, 1988

INVENTOR(S) : Pierre HIRSBRUNNER, et al.

It is certified that error appears in the above-identified patent and that said Letters Patent is hereby corrected as shown below:

On the title page, "ABSTRACT" should be --ABSTRACT OF THE DISCLOSURE--.

Column 1, line 15, "Caffeine" should be indented as beginning a paragraph.

Column 2, line 65, "sujecting" should be --subjecting--.

Column 3, line 3, "it" should be --its--.

Column 3, line 12, insert --EXAMPLES--.

Column 3, line 15, insert a space between "in" and "1".

Column 3, line 21, insert a comma after "charcoal".

Column 4, line 49, after the period, "the" should be --The--.

Signed and Sealed this

Twentieth Day of December, 1988

Attest:

DONALD J. QUIGG

*Attesting Officer*  *Commissioner of Patents and Trademarks*